(12) United States Patent
Townley

(10) Patent No.: US 8,366,785 B1
(45) Date of Patent: Feb. 5, 2013

(54) BASAL THUMB JOINT IMPLANT

(75) Inventor: Charles O. Townley, Port Huron, MI (US)

(73) Assignee: BioPro, Inc., Port Huron, MI (US)

( * ) Notice: Subject to any disclaimer, the term of this patent is extended or adjusted under 35 U.S.C. 154(b) by 1682 days.

(21) Appl. No.: 09/352,472

(22) Filed: Jul. 14, 1999

(51) Int. Cl.
*A61F 2/42* (2006.01)

(52) U.S. Cl. .................................. 623/21.15; 623/21.11

(58) Field of Classification Search ............... 623/21, 623/18, 18.11, 21.11, 21.15, 23.42, 23.44, 623/23.11, 23.15, 22.4, 22.11
See application file for complete search history.

(56) References Cited

U.S. PATENT DOCUMENTS

| | | | | |
|---|---|---|---|---|
| 2,934,065 A | | 4/1960 | Townley | 623/23 |
| 3,314,420 A | * | 4/1967 | Smith et al. | 623/23.3 |
| 3,506,982 A | * | 4/1970 | Steffee | 623/21.16 |
| 4,550,450 A | | 11/1985 | Kinnett | 623/18 |
| 4,955,916 A | * | 9/1990 | Carignan et al. | 623/21 |
| 5,007,932 A | * | 4/1991 | Bekki et al. | 623/21 X |
| 5,047,059 A | | 9/1991 | Saffar | 623/21 |
| 5,405,399 A | * | 4/1995 | Tornier | 623/18 X |
| 5,405,401 A | * | 4/1995 | Lippincott et al. | 623/21.15 |
| 5,507,818 A | * | 4/1996 | McLaughlin | 623/23.42 |
| 5,674,297 A | * | 10/1997 | Lane et al. | 623/21 X |
| 5,702,469 A | | 12/1997 | Whipple et al. | 623/21 |
| 5,782,927 A | * | 7/1998 | Klawitter et al. | 623/21.15 |
| 5,910,171 A | * | 6/1999 | Kummer et al. | 623/18.11 |
| 6,096,084 A | | 8/2000 | Townley | 623/23.12 |
| 6,159,247 A | | 12/2000 | Klawitter et al. | 623/21.15 |

FOREIGN PATENT DOCUMENTS

| | | | |
|---|---|---|---|
| GB | 2239398 | * | 7/1991 |
| WO | 98/19637 | | 5/1998 |

OTHER PUBLICATIONS

*Gray's Anatomy*, 15th Ed., Barnes & Noble, Inc., New York, 1995, pp. 192, 222-225, 237-239.
Ascension Orthopedics, Ascension Implants, CMC, about/contact (www.ascensionortho.com) downloaded Mar. 1, 2005.
Stedman's Medical Dictionary, 24th Edition, Williams & Wilkins, Baltimore, 1982, pp. 125 & 629.
USPTO Patent Full-Text and Image Database, US Pat db, "hemiarthroplasty," Mar. 20, 2008, 77 hits (5 pp.).

(Continued)

*Primary Examiner* — Brian Pellegrino
(74) *Attorney, Agent, or Firm* — Christopher John Rudy; Andrew Joseph Rudy

(57) ABSTRACT

Basal thumb joint implant has a head with a smooth, generally hemispherical, medio-proximally directed, articulating surface, and a generally abrupt, distally directed, truncation thereto; and a stem attached to the head, which arises from the truncation of the head and includes at least one of the following features:
A) a general angle of attachment to the head which is acute in relation to the truncation of the head;
B) a flanged cross-sectional stem profile;
C) an inwardly curved stem;
D) an eccentric head attachment site for the stem.
The implant may be one-piece or modular in construction. The modular basal thumb joint implant, however, which is not necessarily limited by requiring inclusion of the aforesaid additional features A-D, includes a head with a smooth, generally hemispherical, medio-proximally directed, articulating surface, a generally abrupt, distally directed truncation thereto, and a stem trunion-receiving cup in the truncation; and a stem attachable to the head, which stem has intracarpal spike-like distal end, and a proximally directed trunion, which trunion is insertable into the stem trunion-receiving cup of the head. Other digits may be provided with analogous implants, particularly with respect to those digital implants amenable to modularity.

13 Claims, 3 Drawing Sheets

OTHER PUBLICATIONS

Websters New Universal Unabridged Dictionary, Second Deluxe Edition, Dorset & Baber, Cleveland, 1983, pp. 105, 372, 846 & 1375.

Front page of US 6136034 with Information. Disclosure Statement filed in application leading thereto (Jan. 11, 1999).

Front page of US 6299647 with Information Disclosure Statement (pp. 1-2 with attachment) filed in application leading thereto (Mar. 29, 2000).

McKechnie et al. (Eds.), Webster's New Universal Unabridged Dictionary, 2nd Ed., Dorset & Baber, 1983, p. 1817.

Preliminary Amendment with Information Disclosure Statement, pp. 1, 3, 4, with Jan. 6, 1997 FDA letter to BioPro, Inc., in U.S. Appl. No. 09/148,842 (now US 6096084).

Product information, Wright Medical Technology, Orthosphere implant, 1990.

Product information, Wright Medical Technology, Swanson Titanium Great Toe Implant, 1990.

510(k) papers for FDA No. K964472 (complete), 1996.

510(k) papers for FDA No. K030319, 2003.

ASTM F 75-92, 1992.

ASTM F 799-95, 1995.

ASTM F 1377-98, 1998.

ASTM F 1537-94, 1994.

BioPro, Inc., "Physiological Stress Loading Total Hip Replacement System," 1991.

BioPro, Inc., "The Biopro Ceramic Tara," Oct. 1997.

BioPro, Inc., "The TownleyModular Shoulder," Mar. 1998.

Food and Drug Administration letter to BIOPRO giving Section 501(k) approval. Feb. 3, 1997.

Townley, U.S. Appl. No. 09/148,842, filed Sep. 4, 1998, specification.

Wright Medical Technology, "Swanson Titanium Basal Thumb Implant.".

\* cited by examiner

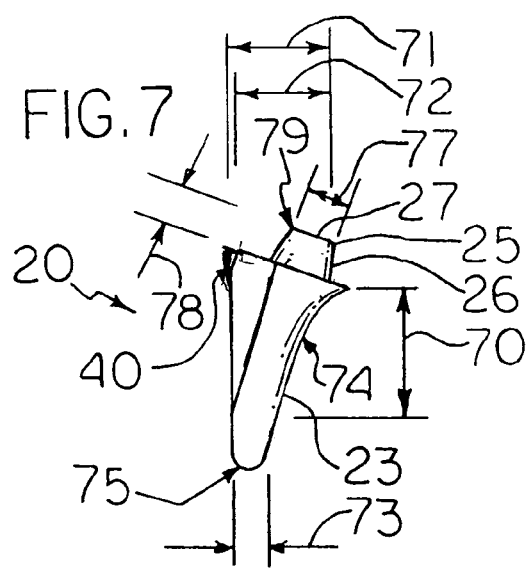
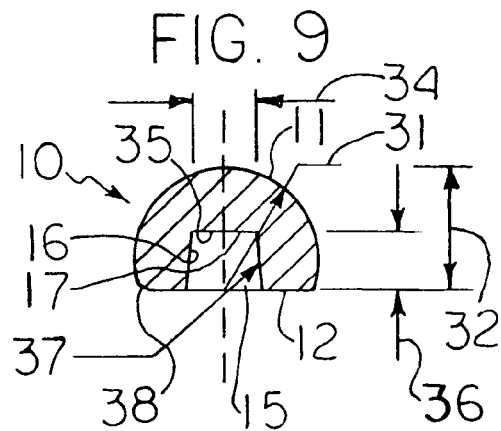
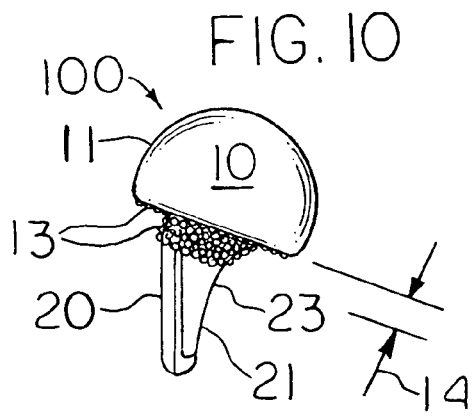
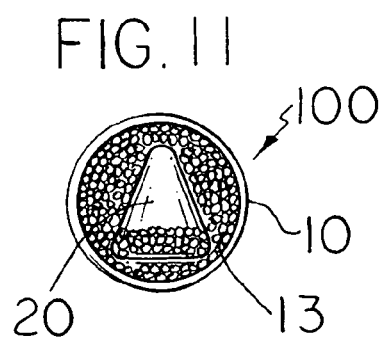
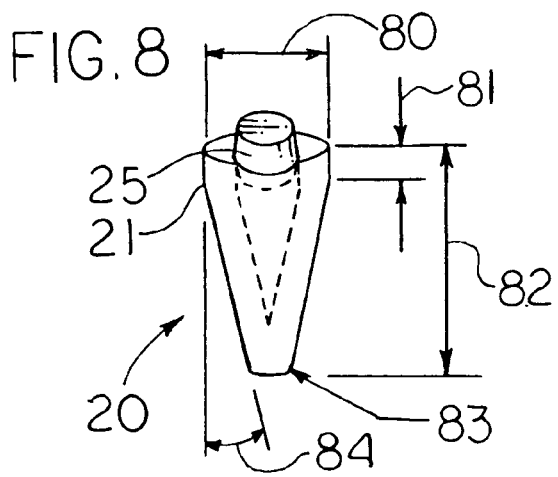
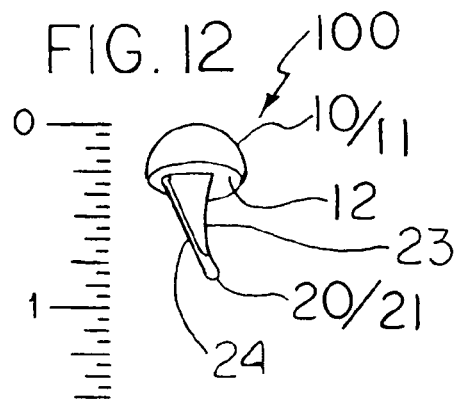

BASAL THUMB JOINT IMPLANT

BACKGROUND TO THE INVENTION

I. Field and Purview of the Invention:

The present invention concerns in particular a one-piece or a modular basal thumb joint implant for the trapeziometacarpal joint, and can also include an extension of the concept of modularity to other digital joints. The implant generally includes head and stem portions, and it has one or more of the following: a generally acute head-stem attachment orientation; a flanged cross-sectional stem profile; an inwardly curved stem; and an eccentric head attachment site for the stem.

II. Prior Art, and Discovered Problems:

Cases of degenerative or post-traumatic arthritis of the trapeziometacarpal joint are known to leave the joint unstable, disfunctional, and painful. In addressing this problem, the Swanson Basal Thumb Joint was developed for use as an adjunct to resection arthroplasty of the joint. The Swanson implant has a generally simple, linearly straight, non-curved stem, which is squarelike in cross-section; when fitted into the intramedullary canal of the first metacarpal bone it is reportedly designed to resist rotation. It also has a convex head, which fits into a jointlike concave surface fashioned in the opposing distal part of the trapezium bone and which reportedly helps restore joint stability and motion. The Swanson joint is a one-piece unit made from unalloyed titanium (ASTM F67). See, the Wright Medical Technology brochure, "Swanson Titanium Basal Thumb Implant."

Problems with the foregoing, however, have been discovered to include 1) the straight, non-anatomical countour of the stem, which (a) reduces the rotational stability of the implant, and (b) induces outward mechanical leveraging of the prosthetic head and the proclivity for lateral dislocation of the replaced joint; 2) the demonstrated inferior tribological characteristics of an articulating titanium surface; and 3) the one-piece construction or non-modularity of the implant, which precludes an ability to "mix and match" component parts, consequently requiring a redundant and costly on-the-shelf inventory of implants to assure the availability of an implant which will provide an appropriate head-stem combination that will produce a precise, individualized dimensional fit of both the head and the intramedullary stem parts of the prosthesis. Also, 4) the square-like configuration of the stem, which is the stabilizing part of the composite implant, provides a gross misfit with the curved and elliptically rounded inner counter of the normal medullary canal, which, as a consequence, requires excessive resectional depletion of endosteal bone to obtain an adequately intimate bone-stem interface fit to assure the long term stability of the implant.

In the hip joint implant field, it is known to employ certain principles of modularity. Certain appropriately sized heads that mate with the acetabular socket may be interchanged for assembly with certain properly sized stems of the femoral component.

SUMMARY OF THE INVENTION

The present invention provides, in one aspect, a basal thumb joint implant comprising a head including a smooth, generally hemispherical, medio-proximally directed, articulating surface, and a generally abrupt, distally directed, truncation thereto; and a stem attached to the head, which arises from the truncation of the head and includes at least one of the following features:

A) a general angle of attachment to the head which is acute in relation to the truncation of the head;
B) a flanged cross-sectional stem profile;
C) an inwardly curved stem;
D) an eccentric head attachment site for the stem.

The implant may be one-piece or modular in construction. The modular basal thumb joint implant, however, which is not necessarily limited by requiring inclusion of the aforesaid additional features A-D, includes a head with a smooth, generally hemispherical, medio-proximally directed, articulating surface, a generally abrupt, distally directed truncation thereto, and a stem trunion-receiving cup in the truncation; and a stem attachable to the head, which stem has intracarpal spike-like distal end, and a proximally directed trunion, which trunion is insertable into the stem trunion-receiving cup of the head. Other digits may be provided with analogous implants, particularly with respect to those digital implants amenable to modularity.

The invention is useful in digital arthroplasty.

Significantly, by the invention, problems in the art are ameliorated if not overcome. The inward (varus) curve of the stem proximally and the eccentric medial placement of the head on the stem avoid the propensity for dislocation of the replaced joint. This anatomically oriented arrangement also permits an unobstructed range of normal pain free motion. The anatomic stem curvature in conjunction with the flanged cross-sectional stem profile, which preferably is a tri-flanged cross-sectional stem profile, provides for a more precise fit with the metacarpal medullary canal anatomy, hence preserving bone stock and assuring optimal long term stability, including near if not complete immovability with respect to rotation, of the implant. The "mix and match" modularity of variably sized heads and stems allows for selective assembly of a composite implant which 1) provides a precise fit for both parts, head and stem, and 2) reduces the on-the-shelf inventory of the composite implant, which, in turn, reduces the cost of the procedure.

Numerous further advantages attend the invention.

DRAWINGS IN BRIEF

The drawings form part of the specification hereof. With respect to the drawings, the following is briefly noted:

FIG. 7 is a medial-lateral view of the stem of the implant of FIG. 4.

FIG. 8 is a lateral view of the stem of FIG. 7.

FIG. 9 is a medial-lateral view of the head of the implant of FIG. 4.

FIG. 10 is a medial-lateral view of a basal thumb joint implant of the invention, otherwise as of FIG. 1 or 4, with a pore-coat thereon.

FIG. 11 is a distal view of the implant of FIG. 10.

FIG. 12 is a view, generally from a medial-lateral perspective, of a basal thumb joint implant of the invention, in a 14.5-millimeter (14.5-mm) finished demonstration model size, with an inwardly curved stem and a more eccentric attachment situs for the stem than would be depicted for the implants of FIGS. 1, 4 & 10, with a rule in inches alongside.

DETAILED DESCRIPTION OF ILLUSTRATIVE EMBODIMENTS OF THE INVENTION

The invention can be further understood by the present detail, which may be read in view of the drawings. Such is to be taken in an illustrative, and not necessarily limiting, sense.

In general, the joint implant of the invention includes a head and a stem. It may be one-piece or modular in construction.

The implant can be made of any suitable material to include biocompatible ceramics, metals, plastics or other suitable material. However, manufacture from a cobalt-containing alloy is beneficially employed since, among other considerations, not the least of which is relative ease of manufacture, a better, more triboligically efficient articular surface can be provided than from the softer titanium, particularly when the implant is of one-piece construction. In modular digital joint implants, the cobalt-containing alloy may be employed for both head and stem components, or, preferably, the cobalt-containing, or other, alloy is employed to make the stem component, and a ceramic is employed to make the head component since, among other considerations, the ceramic can make for an even more smooth articular surface. For example, the implant of the invention which is one-piece or is modular can be machined from a cobalt-containing alloy made in accordance with ASTM F75, or even in accordance with ASTM F799 or ASTM F1537, or further, the modular implants of the invention can have its stem machined from the ASTM F75 cobalt-containing alloy and its head machined from ZIRALLOY ceramic. The head, especially its smooth articulating surface, may be made from another hard, smooth material.

Figure 1:
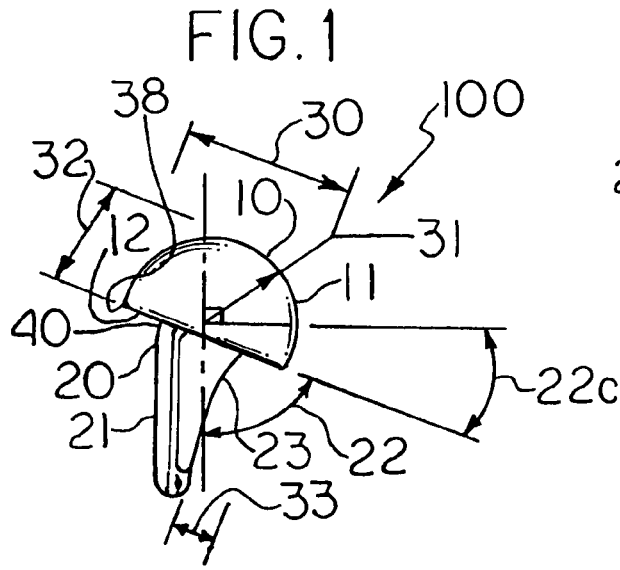
FIG. 1 is a medial-lateral view of a basal thumb joint implant of the invention.
Figure 2:
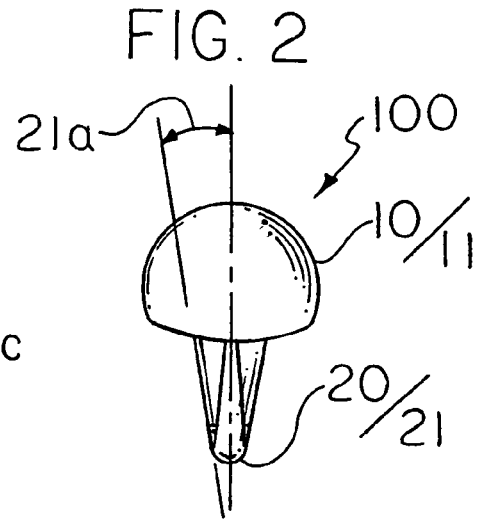
FIG. 2 is a medial view of the implant of FIG. 1.
Figure 5:
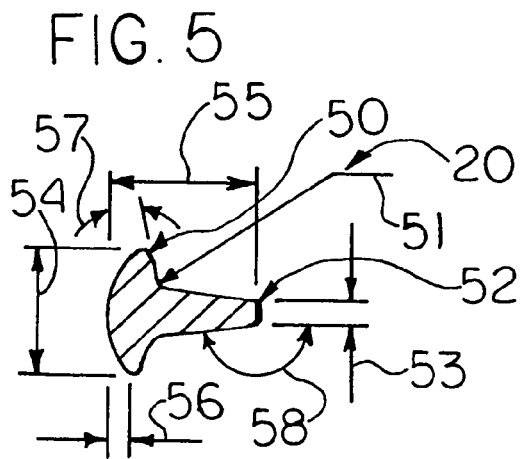
FIG. 5 is a sectional view of the stem of the implant of FIG. 4, taken along 5-5 in FIG. 4.
Figure 3:
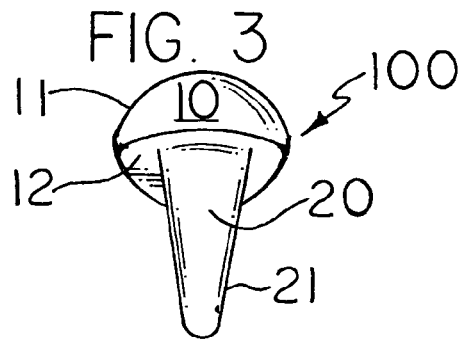
FIG. 3 is a lateral view of the implant of FIG. 1.
Figure 6:
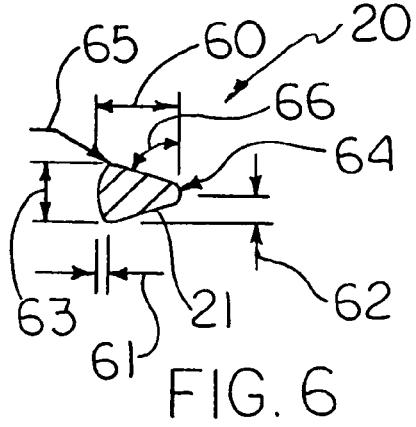
FIG. 6 is a sectional view of the stem of the implant of FIG. 4, taken along 6-6 in FIG. 4.
Figure 4:
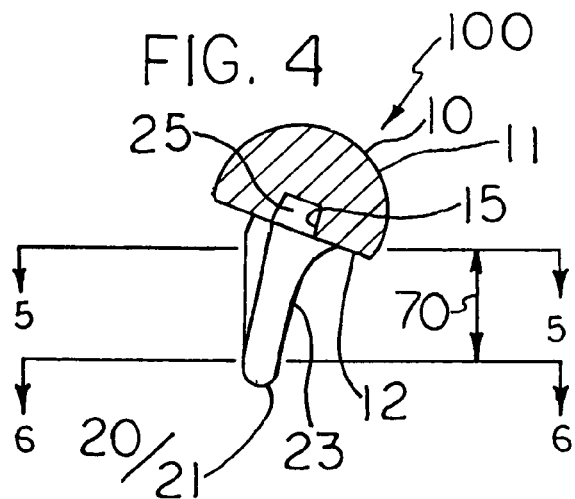
FIG. 4 is a medial-lateral view of a modular basal thumb joint implant of the invention, otherwise generally analogous to an implant such as in FIGS. 1-3, and with its head in section.
Figure 13:
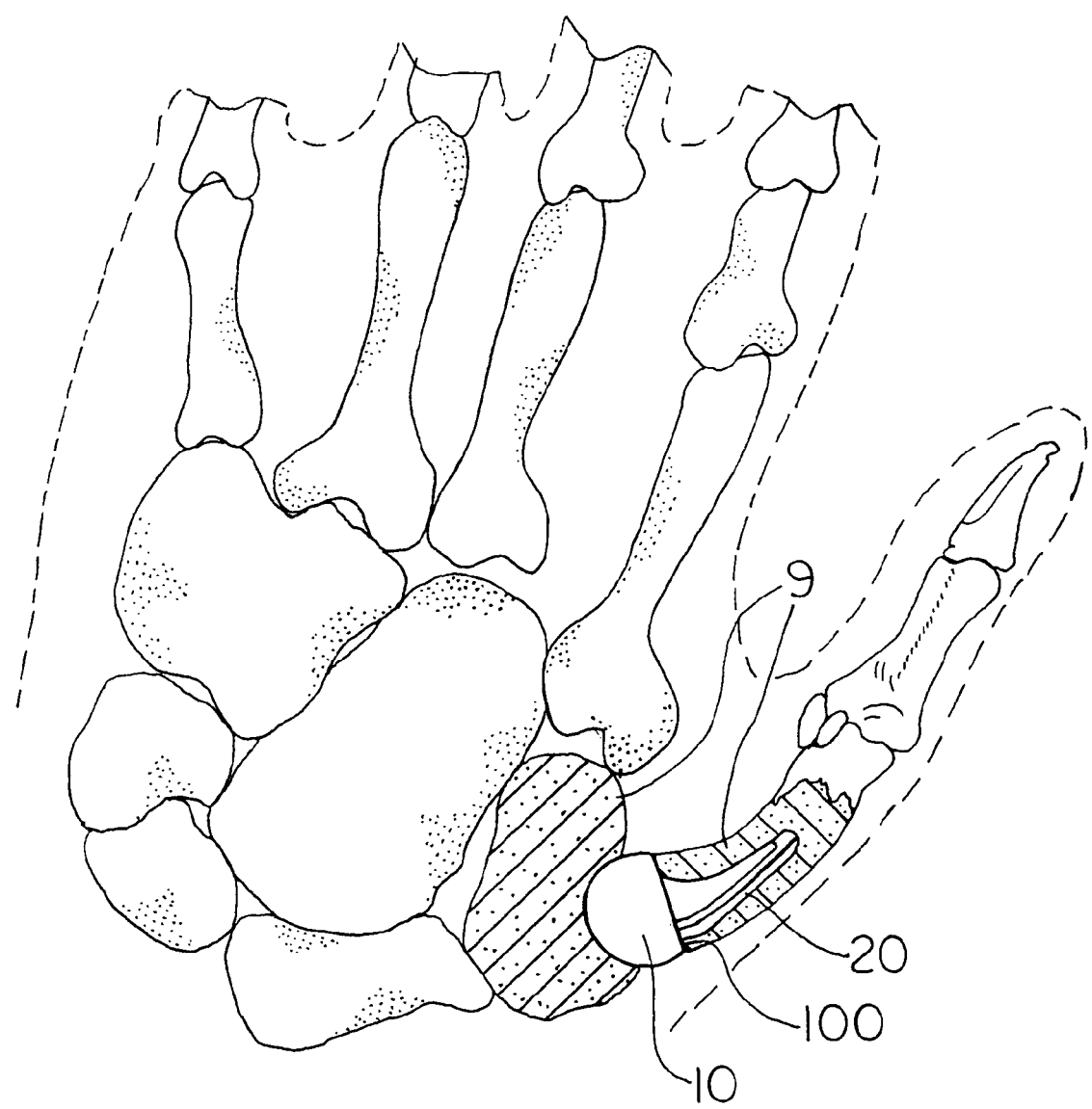
FIG. 13 is a sectional view of the basal thumb joint implant such as of FIGS. 1, 4, 10 and/or 12 in place in the hand.

With respect to the drawings, in FIGS. 1-3, a one-piece implant is depicted; in FIGS. 4-9, modularity is introduced; FIGS. 10 & 11 show pore-coating of an implant; FIG. 12 shows more eccentricity and curvature with respect to the stem, and FIG. 13 generally shows a basal thumb joint implant of the invention implanted in the hand. In general, basal thumb joint implant 100 for mounting in and articulating with a prepared surface of suitable bone stock 9 includes trapezium-mating head 10 and intrametacarpal stem 20.

The head 10 generally includes articulating surface 11, which is smooth, say, to a Number-4 (4√) tolerance, for example, when made of suitable metal, or better, say, if made of suitable ceramic or other suitable material, is generally hemispherical and is proximally directed, and includes truncation 12, which is generally abrupt and distally directed, and may take the form of a flat plane. See, FIGS. 1, 3, 4, 9-13. The truncation 12 may be roughened, say, if of suitable metal as by sand-blasting with glass bead BT-Number-12. In addition to or in lieu of the sand-blasting, porous coating 13 may be present, for example, a 0.020-inch porous coating under the head 10 and around part of the stem 20 near the head, say, for a 0.140-inch distance 14, of the cobalt-chromium-molybdenum powder type to ASTM F-1377-92 specifications may be applied to the implant made from the cobalt-containing alloy. See, FIGS. 10 & 11. The convex articulating surface 11 can register and articulate with a correspondingly concavely prepared part of the distal trapezium bone; the truncation 12 can mate with and reside on a proximally resected mesa of the first metacarpal bone. See, FIG. 13.

In modular joint implants, the head 10 can also include trunion receiving cup 15 which may be, say, cylindrical, conical, frustoconical, or have an elliptical, chordated curvilinear, triangular, rectangular, square, or other cross-section. The cup 15 can include walls 16, which may be tapered as for a Morse taper, and base 17.

The stem 20 generally includes spike 21 may taper from the head 10 to its end distal from the head 10. See, FIGS. 1-8 & 10-13. Thus, among other advantages, the implant 100 may be pressed into place in the metacarpal bone. The stem 20 may be roughened, say, as by sand-blasting with glass bead BT-Number-12. In addition to or in lieu of the sand-blasting, the pore-coating 13 may be applied, especially about the more proximally directed portions of the stem 20. See, FIGS. 10 & 11. The stem/spike 20/21 may have a general angle 22 of attachment to the head which is acute, for instance, about from sixty-five to seventy-five, say, about seventy, degrees in relation to the truncation 12 of the head 10, which may yield complementary angle 22$c$. The stem/spike 20/21 may have a flanged cross-sectional stem profile. For example, the flanged stem profile may have a tri-flanged cross section such as provided by being generally T-shaped, especially about its more proximal positions. See, e.g., FIG. 5. The flanged stem profile may taper to a more generally triagonally shaped cross-section, especially about its more distal positions. See, e.g., FIG. 6. Accordingly, the spike 21, which may be termed an intracarpal spike-like stem or appendage, can taper toward its distal end, for example, at half angle 21$a$ as follows: 13-mm and 14-mm sizes, 10-degree half angle; 16-mm size, 12-degree half angle; 17.5-mm and 19-mm sizes, 13-degree half angle. Thus, not only can the stem 20 be readily inserted into the digital bone stock which can be more easily prepared to receive such a shape and conserve bone in the procedure but also the flanges can more strongly hold the stem in the bone. The stem/spike 20/21 may be inwardly curved with concave 23 and/or convex 24 components, and/or have an eccentric attachment site, offset from the center of the head 10. See, e.g., FIGS. 1, 4, 7, 10 & 12. Preferably, however, the basal thumb implant 100 generally includes all of such features. Thus, anatomical cooperation and normal functioning can better ensue.

With the modular basal thumb joint implant 100, the stem is attachable to the head. Its stem 20 can have not only the intracarpal spike-like appendage 21, which, again, may be tapered toward its distal end, but also a proximally directed trunion 25, which itself may be, say, cylindrical, conical, frustoconical, or have an elliptical, chordated curvilinear, triangular, rectangular, square, or other cross-section. The trunion 25 can include walls 26, which may be tapered as for the Morse taper, and cap 27. The trunion 25 is insertable into the stem trunion receiving cup 15 of the modular head 10, and, in general, its walls 26 and cap 27 suitably correspond to the walls 16 and base 17 of the modular head 10. See, FIGS. 4, 7-9.

Actual dimensions of the implant may vary according to needs or desire's. For example, basal thumb joint implants 100 can have for its head 10 with noted diameter 30 (size in millimeters (mm)) the dimensions (listed in inches) which follow:

| | 13-mm | 14.5-mm | 16-mm | 17.5-mm | 19-mm |
|---|---|---|---|---|---|
| Spherical radius 31 (FIG. 1) | 0.250 | 0.281 | 0.313 | 0.344 | 0.375 |

-continued

|  | 13-mm | 14.5-mm | 16-mm | 17.5-mm | 19-mm |
|---|---|---|---|---|---|
| Spherical radius 31 (FIG. 9) | 0.250 | 0.281 | 0.312 | 0.344 | 0.375 |
| Head height 32 (FIG. 1) | 0.289 | 0.320 | 0.373 | 0.413 | 0.455 |
| Head height 32 (FIG. 9) | 0.290 | 0.331 | 0.372 | 0.414 | 0.455 |
| Distance 33 as cast (FIG. 1) | 0.170 | 0.200 | 0.230 | 0.225 | 0.250. |

In addition, the modular head 10 can have its stem trunion receiving cup 15 include the following dimensions (FIG. 9): base diameter 34, 0.1514"; wall-base radius 35, 0.015"; cup depth 36, 0.150"; wall half angle taper 37, 2.8625-degrees. Also, with respect to FIGS. 1 & 9, the heads 10 can have a 0.020-inch (") truncation radius 38. As well, the dimensions of the stem 20 can vary as necessary or desired, for example, referring to FIG. 1, radius 40 can be for the 13-mm size implant, 0.252"; 14.5-mm and 16-mm, 0.315"; 17.5-mm and 19-mm, 0.394"; referring to FIGS. 5-8, the following dimensions (in inches) may obtain:

|  | Small | Medium | Large |
|---|---|---|---|
| Radius 40 (FIG. 7) | 0.2522 | 0.3152 | 0.394 |
| Radius 50 (FIG. 5) | 0.0145 | 0.0181 | 0.0226 |
| Radius 51 (FIG. 5) | 0.0198 | 0.0248 | 0.031 |
| Radius 52 (FIG. 5) | 0.0282 | 0.0352 | 0.044 |
| Length 53 (FIG. 5) | 0.0554 | 0.0693 | 0.0866 |
| Length 54 (FIG. 5) | 0.2522 | 0.3152 | 0.394 |
| Width 55 (FIG. 5) | 0.0399 | 0.0499 | 0.0624 |
| Width 56 (FIG. 5) | 0.2522 | 0.3152 | 0.394 |
| Width 60 (FIG. 6) | 0.1022 | 0.1246 | 0.1557 |
| Width 61 (FIG. 6) | 0.0162 | 0.0197 | 0.0246 |
| Length 62 (FIG. 6) | 0.0201 | 0.0245 | 0.0306 |
| Length 63 (FIG. 6) | 0.1022 | 0.1247 | 0.1557 |
| Radius 64 (FIG. 6) | 0.0114 | 0.0139 | 0.0174 |
| Radius 65 (FIG. 6) | 0.0058 | 0.0071 | 0.0089 |
| Height 70 (FIGS. 4, 7) | 0.3547 | 0.4434 | 0.5542 |
| Width 71 (FIG. 7) | 0.2522 | 0.3152 | 0.394 |
| Width 72 (FIG. 7) | 0.2370 | 0.2962 | 0.3702 |
| Width 73 (FIG. 7) | 0.0997 | 0.1246 | 0.1557 |
| Radius 74 (FIG. 7) | 0.5659 | 0.7074 | 0.8842 |
| Radius 75 (FIG. 7) | 0.0498 | 0.0623 | 0.0799 |
| Radius 76 (FIG.7) | 0.2522 | 0.3152 | 0.394 |
| Length 80 (FIG.8) | 0.2522 | 0.3152 | 0.394 |
| Height 81 (FIG.8) | 0.0862 | 0.1078 | 0.13475 |
| Height 82 (FIG.8) | 0.5165 | 0.6456 | 0.807 |
| Radius 83 (FIG.8) | 0.0416 | 0.052 | 0.065. |

In addition, there may be 11-degree angle 57 and 170-degree angle 58 (FIG. 5); 62-degree angle 66 (FIG. 6); 0.151-inch (") trunion reference diameter 77 and trunion height 78 of 0.125" for the trunion 25, which may have a 0.010"×45-degree circumferential top chamfer 79 and a 2-degree 47-minute 45-second half angle taper to the wall 26 (FIG. 7); and a 12-degree angle 84 (FIG. 8).

The implant is implanted at the discretion of the surgeon. Surgical cement such as polymethylmethacrylate may be employed.

CONCLUSION

The present invention is thus provided. Various features, subcombinations and combinations can be practiced with or without reference to other features, subcombinations or combinations in the practice of the invention, and numerous adaptations and modifications can be effected within its spirit, the literal claim scope of which is particularly pointed out as follows:

I claim:

1. A one-piece, basal thumb joint implant comprising a head including a single, smooth, generally hemispherical, media-proximally directed articulating surface, and a generally abrupt, distally directed, planar end thereto, said generally hemispherical articulating surface being continuous as to its sphericity and uninterrupted up to the generally planar end; and a distally directed stem protruding from and monolithic with the head, which stem arises from and makes a junction with the generally planar end of the head, wherein the implant includes the following features:
   (A) a general angle of junction of the stem with the head, which is about from sixty-five to seventy-five degrees in relation to the generally planar end of the head;
   (B) a tri-flanged cross-sectional stem profile;
   (C) an inwardly curved stem; and
   (D) an eccentric head junction site for the stem;
   wherein the inward curve of the stem and the eccentric placement of the head on the stem avoid a propensity for dislocation of a replaced joint; such an anatomically oriented arrangement also permits an unobstructed range of normal pain free motion; and the curved stem in conjunction with the flanged cross-sectional stem profile provides for a precise fit with metacarpal medullary canal anatomy, hence preserving bone stock and assuring optimal long term stability, including near if not complete immovability with respect to rotation, of the implant.

2. The implant of claim 1, wherein the general angle of the junction of the stem with the head is about seventy degrees in relation to the generally planar end of the head, and the stem profile generally is T-shaped and tapers from the head to a distal end of the stem such that the stem can be readily inserted into the metacarpal bone stock.

3. The implant of claim 1, which is made of a cobalt-containing alloy.

4. The implant of claim 1, which is made of a suitable ceramic material.

5. The implant of claim 1, which includes for bone interface a porous coating.

6. A basal thumb joint implant comprising a head including a single, smooth, medic-proximally directed, articulating surface that is defined by a constant spherical radius and is greater than a hemisphere, and a generally abrupt, distally directed, planar end to the head, which defines an end to said articulating surface, said articulating surface being continuous as to its sphericity and uninterrupted up to the end of said articulating surface so that said articulating surface and the generally planar end define a truncated ball; and a stem projecting from the head, which arises from the generally planar end to the head and includes the following features:
   (A) a general angle of projection from the head, which is acute in relation to the generally planar end to the head;
   (B) a flanged cross-sectional stem profile;
   (C) an inwardly curved stem;
   (D) an eccentric head junction site for the stem;
   wherein said implant has its head of a size for mounting in and articulating with a correspondingly concavely prepared surface of trapezium bone stock; its stem of a size for intramedullary insertion in metacarpal bone stock; the inward curve of the stem and the eccentric placement of the head on the stem avoid a propensity for dislocation of a replaced joint; such an anatomically oriented arrangement also permits an unobstructed range of normal pain free motion; and the curved stem in conjunction with the flanged cross-sectional stem profile provides for a precise fit with metacarpal medullary canal anatomy, hence preserving bone stock and assuring optimal long term stability, including near if not complete immovability with respect to rotation, of the implant.

7. The implant of claim 6, which is made of a cobalt-containing alloy.

8. The implant of claim 6, which is made of a suitable ceramic material.

9. A one-piece, basal thumb joint implant comprising a head including a single, smooth, generally hemispherical, medio-proximally directed, articulating surface, and including a generally abrupt, distally directed, planar end to the head, which defines an end to said generally hemispherical articulating surface, said generally hemispherical articulating surface being continuous as to its sphericity and uninterrupted up to the end of the generally hemispherical articulating surface; and a distally directed stem protruding from and monolithic with the head, which stem arises from and makes a junction with the generally planar end to the head, wherein the implant includes the following features:
   (A) a general angle of junction of the stem with the head, which is about from sixty-five to seventy-five degrees in relation to the generally planar end to the head;
   (B) a tri-flanged cross-sectional stem profile;
   (C) an inwardly curved stem;
   (D) an eccentric head junction site for the stem; and
   (E) at least one of the following features:
      (i) a roughened, sand-blasted surface for the generally planar end to the head; and
      (ii) a roughened, sand-blasted surface for the stem;
wherein the inward curve of the stem and the eccentric placement of the head on the stem avoid a propensity for dislocation of a replaced joint; such an anatomically oriented arrangement also permits an unobstructed range of normal pain free motion; and the curved stem in conjunction with the flanged cross-sectional stem profile provides for a precise fit with metacarpal medullary canal anatomy, hence preserving bone stock and assuring optimal long term stability, including near if not complete immovability with respect to rotation, of the implant.

10. The implant of claim 9, wherein the general angle of the junction of the stem with the head is about seventy degrees in relation to the generally planar end to the head, and the stem profile generally is T-shaped and tapers from the head to a distal end of the stem such that the stem can be readily inserted into the metacarpal bone stock.

11. The implant of claim 10, which is made of a cobalt-containing alloy.

12. The implant of claim 10, which is made of a suitable ceramic material.

13. A basal thumb joint implant comprising a head including a single, smooth, generally hemispherical, medio-proximally directed, articulating surface, and a generally abrupt, distally directed, planar end to the head, which defines an end to said articulating surface, said articulating surface being continuous as to its sphericity and uninterrupted up to the end of said articulating surface so that said articulating surface defines a truncated ball of a shape that is from substantially hemispherical to greater than substantially hemispherical; and a stem projecting from the head along an axis, which arises from the generally planar end to the head and includes the following features:
   (A) a general angle of projection from the head, which is acute in relation to the generally planar end to the head so as to help align the stem in intramedullary bone stock that has been resected substantially normal to its proximal end;
   (B) a flanged cross-sectional stem profile, which, when taken in cross-section perpendicularly to the stem, is in a tri-flange shape, with three flanges without notches extending distally on the stem, which helps provide for a precise fit with metacarpal medullary canal anatomy, hence preserving bone stock and assuring optimal long term stability, including near if not complete immovability with respect to rotation, of the implant;
   (C) an inwardly curved stem so as to help avoid a propensity for dislocation of a replaced joint, and which helps to provide for a precise fit with metacarpal medullary canal anatomy, hence preserving bone stock and assuring optimal long term stability, including near if not complete immovability with respect to rotation, of the implant; and
   (D) an eccentric head junction site for the stem so as to help avoid a propensity for dislocation of a replaced joint;
wherein said implant has its head of a size for mounting in and articulating with a correspondingly concavely prepared surface of trapezium bone stock; its stem of a size for intramedullary insertion in the metacarpal bone stock of the thumb; and such feature(s) of an anatomically oriented arrangement help(s) permit an unobstructed range of normal pain free motion.

* * * * *